United States Patent [19]

Ohata et al.

[11] Patent Number: 4,853,436

[45] Date of Patent: Aug. 1, 1989

[54] GRAFT POLYMERIZATION OF SUBSTITUTED STYRENE POLYMERS HAVING PENDANT VINYLIDENE GROUPS

[75] Inventors: Masatoshi Ohata, Sakai; Koichi Tsutsui, Tanabecho; Ikedal Shoji, Hirakata; Teruo Fujimoto, Nagaoka, all of Japan

[73] Assignee: Nippon Paint Co., Ltd., Osaka, Japan

[21] Appl. No.: 157,560

[22] Filed: Feb. 19, 1988

[30] Foreign Application Priority Data

Feb. 20, 1987 [JP] Japan .................................. 62-38238

[51] Int. Cl.[4] .................... C08F 279/06; C08F 279/04; C08F 279/02; C08F 279/00
[52] U.S. Cl. ..................................... 525/244; 525/250; 525/259; 525/288; 525/310; 525/315; 525/316
[58] Field of Search ............... 525/242, 250, 244, 259, 525/288, 310, 315, 316

[56] References Cited

U.S. PATENT DOCUMENTS 3,925,511 12/1975 Loveless .............................. 525/272
4,340,690 7/1982 Lal ....................................... 525/250
4,707,521 11/1987 Esneault .............................. 525/250

OTHER PUBLICATIONS

Braun et al, Chem. Abstracts, 71(2)3696h; 1969.

*Primary Examiner*—John C. Bleutge
*Assistant Examiner*—David Buttner
*Attorney, Agent, or Firm*—Millen, White & Zelano

[57] ABSTRACT

A graft copolymer having a plurality of polymer side chains is disclosed. The starting backbone polymer is a homopolymer or copolymer of a styrene derivative having a pendant vinylidene group on the benzene ring. The graft copolymer may be produced by metallizing said backbone polymer with an alkali metal and then polymerizing an ethylenically unsaturated monomer in the presence of the metallized polymer as an anionic polymerization initiator.

8 Claims, No Drawings

GRAFT POLYMERIZATION OF SUBSTITUTED STYRENE POLYMERS HAVING PENDANT VINYLIDENE GROUPS

BACKGROUND OF THE INVENTION

This invention relates to a substituted styrene polymer having a plurality of pendant vinylidene groups and also to a graft copolymer derived from said substituted styrene polymer.

As is well-known, the viscosity of a polymer substance is a function of its molecular weight. It is also well-known that branched polymers having star- or comb-like configuration generally have a viscosity lower than straight chain linear polymers having corresponding molecular weights.

Recently, strong demands exist for high-solids coating compositions. In order to achieve this, it is necessary to use low molecular weight vehicle resins so that the resulting coating formulations have a suitable viscosity for application even at high solid contents. However, the use of low molecular weight resins often suffer from certain disadvantages such as decrease in workability and film properties. Since the viscosity of branched polymers is significantly lower than the viscosity of straight chain linear polymers having corresponding molecular weights, their potential as a vehicle resin for formulating high-solids coating compositions is of great interest.

In our Japanese Patent Application No. 239,223, there is disclosed a method for producing a graft copolymer comprising the steps of metallizing poly-(p-methylstyrene)(PPMS) or styrene/p-methylstyrene/styrene ternary block copolymer (SMS) with n-butyl lithium/tetramethylethylenediamine, reacting the resulting pseudogels (precipitates) of metallized polymer with a vinylidene monomer such as 1,1-diphenylethylene (DPE) to form an adduct, and graft-polymerizing acrylic monomers using said adduct as an initiator. This method is advantageous in that the adduct is soluble in conventional inert organic solvents and that undesirable side reactions such as carbonyl addition to the metallized reaction site do not occur.

However, it has been discovered that the resulting product often contains a significant amount of homopolymers of said acrylic monomers. This is because the starting PPMS or SMS is not fully metallized and thus remaining unreacted metallizing agent serves as an initiator of the homopolymerization of acrylic monomers. This side reaction may be avoided by thoroughly washing the metallized polymer with an organic solvent before reacting with the vinylidene monomer to remove unreacted metallizing agent.

It would be desirable for the synthesis of a graft copolymer by the anion polymerization technique to have a metallized polymer initiator which is soluble in a variety of innert organic solvents and which has a high metallizing efficiency (preferably as nearly as 100%) and a high initiator capability. It is also desirable for the graft polymerization to be a living polymerization.

The present invention concerns the provision of a substituted styrene polymer which may give a metallized polymer initiator having the above-described characteristics. The invention also concern the provision of a new graft copolymer having a plurality of side chains grafted to said substituted styrene polymer.

SUMMARY OF THE INVENTION

According to one aspect of the present invention, there is provided a polymer consisting essentially of 0.1 to 100 mole% of a recurring unit of the formula:

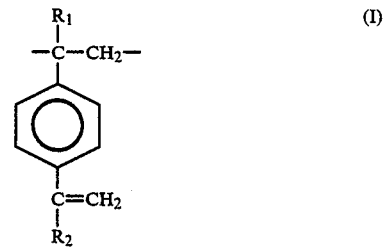

wherein $R_1$ is H or $C_1$-$C_4$ alkyl; and $R_2$ is $C_2$-$C_{10}$ alkyl or alkoxy, unsubstituted or substituted phenyl, or tri-($C_1$-$C_4$ alkyl)silyl; and the balance of a recurring unit of the formula:

wherein $R_1$ is as defined and $R_3$ is $C_1$-$C_4$ alkyl or alkoxy, or unsubstitued or substituted phenyl; a recurring unit of the formula:

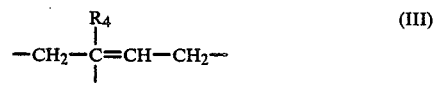

wherein $R_4$ is H, $C_1$-$C_4$ alkyl or halogen; a position isomer of the unit of the formula (III); or a mixture of said units (II), (III) or its position isomer; said polymer having a number average molecular weight of 1,000 to 1,000,000.

In the second aspect of the present invention, the above polymer is produced by anion- or cation-polymerizing 0.1 to 100 mole% of a monomer of the formula:

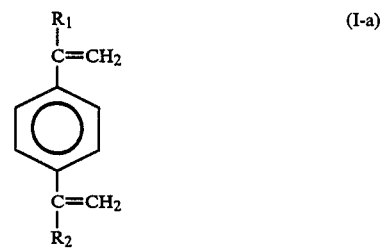

wherein $R_1$ and $R_2$ are as defined, and the balance of a monomer of the formula:

a monomer of the formula:

wherein $R_4$ is as defined or a mixture of said monomers (II-a) and (III-a).

In a further aspect of the invention, there is provided a graft copolymer having a backbone polymer segment and a plurality of polymer side chains grafted thereto, wherein said backbone polymer is the afore-mentioned polymer having a plurality of vinylidene groups on the benzene ring, and wherein each of said polymer side chains is a polymer of an ethylenically unsaturated monomers capable of anion polymerization having a number average molecular weight from 500 to 1,000,000 per chain, said polymer side chains being grafted to said backbone polymer at said plurality of pendant vinylidene groups.

In a still further aspect of the present invention, the above graft copolymer may be produced by the steps of reacting the afore-mentioned polymer having a plurality of pendant vinylidene groups with a compound of the formula $MR_4$, wherein M is a metal of group Ia in the periodic table and $R_5$ is a hydrocarbon radical to metallize said pendant vinylidene groups, graft-plymerizing a monomer capable of anion polymerization to each metallized site of said starting polymer until each grafted polymer chain has a number average molecular weight of 500 to 1,000,000. Alternatively, said graft coplymer may be produced by first preparing a living polymer having a number average molecular weight of 500 to 1,000,000 and then coupling the living terminal of said living polymer to said pendant vinylidene groups of the starting backbone polymer.

Advantageously, the terminals of said polymer side chains of the resulting graft copolymer may be chemically modified to have a plurality functional groups capable of crosslinking.

The present invention has a number of important advantages over the prior art graft copolymers. The pendant vinylidene groups possessed by the starting backbone polymer may be metallized almost quantitatively. Since the polymer is metallized in the vicinity of a bulky substituent, the metallized polymer is less liable to association because of steric hinderance. It is for this reason that the metallized polymer is soluble in most of nonpolar organic solvents. The steric hinderance also serves to suppress undesirable side reactions such as carbonyl addition to the metallized site. All of the above features lead to a high yield of desired graft copolymer.

The starting backbone polymer itself may be obtained in a high yield and its metallization may be performed almost quantitatively. This permits the backbone polymer and its metallized product to be purified very easily and thus simplifies the entire operation.

DETAILED DISCUSSION

Preparation of Starting Backbone Polymer

Examples of monomers of the formula I-a include 1-phenyl-1-(4-vinylphenyl)ethylene, 1-(4-methylphenyl)-1-(4-vinylphenyl)ethylene, 1-(4-propylphenyl)-1-(4-vinylphenyl)ethylene, 1-trimethylsilyl-1-(4-vinylphenyl)ethylene and the like.

Examples of monomers of the formula II-a include styrene, p- or m-methylstyrene, p-chlorostyrene, p-methoxystyrene, α-methyl-styrene, isobutene and the like.

Examples of diene monomers of the formula III-a include butadiene, isoprene, chloroprene, t-butylbutadiene, and the like. These diene monomers may be incorporated in the polymer chain through 1,4-, 1,2- or 3,4- (except for $R_4=H$) bond.

The starting backbone polymer may be the homopolymer of a monomer of the formula I-a. Up to 99.0 mole% thereof may be replaced by monomer II-a, III-a or a combination these monomers.

The backbone polymer may be produced by anion- or cation polymerizing the above monomer or monomers by per se known methods.

Examples of usable anion polymerization initiators include n-butyl lithium, sec-butyl lithium, ter-butyl lithium, naphthalene sodium, cumyl potassium, cumyl cesium and the like. The quantity of the initiator in this step is not critical.

The anion polymerization may be carried out at a temperature of $-100°$ C. to $+80°$ C., more preferably from $-80°$ C. to $+50°$ C. in the atmosphere of an inert gas or under high vacuum in an inert organic solvent.

Examples of usable organic solvents include ethers such as diethyl ether, methyl ethyl ether or tetrahydrofuran; aromatic hydrocarbons such as benzene, toluene, xylene or ethylbenzene; and aliphatic hydrocarbons such as pentane, hexane, heptane or cyclohexane.

Examples of usable cation polymerization initiators include protonic acids such as perchloric acid, acetyl perchloric acid, sulfuric acid, p-toluenesulfonic acid or trifluoromethanesulfonic acid, co-catalyst-containing metal halide initiators such as aluminum chloride, boron trifluoride or tin tetrachloride; and co-catalyst-containing organometallic initiators such as triethylaluminum, diethylaluminum chloride or ethylaluminum dichloride.

The cation polymerization may be carried out in the atmosphere of an inert gas or under high vacuum in an inert organic solvent.

Examples of usable organic solvents include aromatic hydrocarbons such as benzene, toluene, xylene, ethylbenzene or chlorobenzene; aliphatic hydrocarbons such as pentane, hexane, heptane, cyclohexane; and halogenated aliphatic hydrocarbons such as carbon tetrachloride, chloroform, methylene chloride or trichloroethane. Combinations of two or more solvents may also be used.

The reaction temperature ranges between $-100°$ C. and $+80°$ C., preferably between $-80°$ C. and $0°$ C. Since higher temperatures tend to promote the crosslinking reaction of pendant vinylidene groups, the lower the better within the above range.

The reaction time may vary from 1 minute to 72 hours depending upon the reaction temperature. Too long reaction time tends to induce the crosslinking reaction of pendant vinylidene groups and is therefore undesirable.

The quantity of initiator may range between 0.05 to 100 mmols per mole of the monomer. Too small quantities may result in a prolonged reaction time. Conversely, an excessive amount is no economical and requires undue steps for removing the catalyst after use.

The resulting polymers having a plurality of pendant vinylidene groups on the benzene ring are soluble in most of conventional organic solvents. They may be used as the starting backbone polymer in the synthesis of the graft copolymer to be discussed hereinafter. Also, they may be modified by reacting the pendant vinylidene group with various reagents to obtain a variety of functional polymers.

Graft Copolymerization

For use as a starting backbone polymer, the above polymer preferably has a number average molecular weight of 1,000 to 1,000,000. The polymer is first metallized by reacting with an alkali metal organic compound of the formula $MR_4$, wherein M and $R_4$ are as defined hereinbefore.

Examples of metallic compounds include n-butyl lithium, sec-butyl lithium, tert-butyl lithium, cumyl potassium, cumyl cesium and the like. The quantity of metallizing agent is not critical provided that it is not large excess relative to the number of pendant vinylidene groups. When the alkali metal organic compound is used nearly on equimolar basis relative to the pendant vinylidene groups, it is preferable to use 0.5 to 20 moles, more preferably 2 to 10 moles per mole of the metallic compound of a tertiary amine such as triethylamine or N-methylpyrrolidine in conjuction with the alkali metal organic compound. This is effective to prevent the metallized polymer from gelling when it contains residual vinyl groups.

The metallizing reaction may be carried out at a temperature of $-80°$ C. to $+80°$ C., preferably $-20°$ C. to $+30°$ C. in the atmosphere of an inert gas or under high vacuum in an inert organic solvent. Examples of usable solvents include ethers such as dimethoxyethane, diethyl ether or tetrahydrofuran, and aromatic hydrocarbons such as benzene, toluene, xylene or ethylbenzene. The concentration of the polymer in these solvents is not critical but preferably ranges between 2 and 8 w/v %.

The number of grafting sites per molecule may be selectively controlled by adjusting the quantity of the alkali metal organic compound. The resulting metallized polymer may be used as a polymeric anion polymerization initiator for graft-copolymerizing suitable monomers thereto.

Examples of usable monomers are acrylic or methacrylic monomers such as methyl acrylate, ethyl acrylate, n-butyl acrylate, isobutyl acrylate, phenyl acrylate, benzyl acrylate, acrylonitrile and corresponding esters and nitrile of methacrylic acid; styrene or its derivatives such as styrene, m- or p-methylstyrene or α-methylstyrene; and diene monomers such as butadiene, isoprene or 1,4-hexadiene. Of course, these monomers should not have such a functional group that reacts with the polymeric anion polymerization initiator to inhibit the polymerization reaction. When monomers having a polar group such as acrylic or methacrylic esters are used, an amount of an alkali metal alkoxide may be added to the reaction mixture to decrease its viscosity and also to prevent gellation. When the monomer is an acrylic or methacrylic ester, the addition of an alkali metal alkoxide serves to increase the proportion of isotactic polymer segments in the side chains.

The quantity of the alkali metal alkoxide may be up to 20 times, preferably up to 10 times in mole per each metallized site of the backbone polymer. Examples of usable alkali metal alkoxides include lithium methoxide, lithium ethoxide, lithium propoxide, lithium isopropylbenzyloxide, sodium isopropylbenzyloxide, lithium stearyloxide, sodium stearyloxide, lithium benzyloxide, sodium methoxide, potassium propoxide sodium benzyloxide and the like. These alkali metal alkoxides are not capable of initiating the polymerization of acrylic or methacrylic esters.

The graft polymerization reaction may be carried out at a temperature of $-100°$ C. to $+80°$ C. in the atmosphere of an inert gas or under high vacuum in the inert organic solvent as used in the metallizing reaction. When acrylic monomers are used, lower temperatures within the above range are preferable for preventing undesirable side reactions such as cyclization.

The growth of side chain polymers takes place as a living polymerization reaction. When a number average molecular weight of 500 to 1,000,000 is obtained for each side chain, the living growth terminal of each side chain is deactivated. The molecular weight of the side chain may be preselected by varying moles of grafting monomers per each metallized site of the backbone polymer.

Deactivation of the living growth terminals of side chains may be effected by adding a suitable protic solvent such as methanol. Alternatively, the living growth terminals may be reacted with an appropriate exogeneous reagent to introduce a function group such as amino, hydroxy, carboxyl, halo, mercapto, sulfony, epoxy and the like.

Examples of reagents used for introducing hydroxy function to the side chain terminal include aldehydes such as formaldehyde, acetaldehyde, n-butylaldehyde, chloral, propionaldehyde, isobutylaldehyde, n-valeraldehyde, n-capraldehyde, n-heptaldehyde or stearylaldehyde; ketones such as acetone, methylethylketone or diethylketone; alkylene oxides and derivatives thereof such as ethylene oxide, propylene oxide, trimethylene oxide, butylene oxide, pentylene oxide, cyclohexylene oxide or styrene oxide. Oxygen gas may be used to introduce a hydroxy function.

Carbon dioxide may be reacted to introduce a caboxyl function.

Imines such as ethyleneimine, propyleneimine or cyclohexeneimine may be used for introducing an amino function to the side chain terminals.

Carbon disulfide, ethylenesulfide, propylene-sulfide and elementary sulfur may be used for introducing a mercapto function. Sulfuryl chloride and epichlorhydrine may be used for introducing sulfonyl and epoxide function, respectively.

The time required for the completion of the above reaction up to the introduction of functional groups to the side chain terminals may vary between one minutes and 72 hours depending upon the nature of particular reactants, reaction temperature and the like.

According to another embodiment of the present invention, the side chain polymer may be prepared separately in the form of a living polymer and then coupled to the pendant vinylidene groups present in the backbone polymer.

In the synthesis of the living polymer, the same alkal metal organic compound of the formula $MR_4$ as used in the previous embodiment may be used as a polymerization initiator.

Examples of usable monomers are acrylic or methacrylic monomers such as methyl acrylate, ethyl acrylate, n-butyl acrylate, isobutyl acrylate, phenyl acrylate, benzyl acrylate, acrylonitrile, and corresponding esters and nitrile of methacrylic acid; styrene or its derivatives such as styrene, m- or p-methylstyrene or α-methylstyrene; and diene monomers such as butadiene, isoprene or 1,4-hexadiene. When monomers having a polar group such as acrylic or methacrylic esters are used, an amount of an alkali metal alkoxide may be added to the reaction mixture to decrease its viscosity and also to prevent gellation. When the monomer is an acrylic or methacrylic ester, the addition of an alkali metal alkoxide serves to increase the proportion of isotactic polymer segments in the side chains.

The quantity of the alkali metal alkoxide may be up to 20 times, preferably up to 10 times in mole per each mole of the initiator alkali metal compound. Examples of usable alkali metal alkoxides include lithium methoxide, lithium ethoxide, lithium propoxide, lithium isopropylbenzyloxide, sodium isopropylbenzyloxide, lithium stearyloxide, sodium stearyloxide, lithium benzyloxide, sodium methoxide, potassium propoxide sodium benzyloxide and the like.

The living polymerization reaction may be carried out at a temperature of $-80°$ C. to $100°$ C. in the atmosphere of an inert gas or under high vacuum in an inert organic solvent as used in the previous embodiment.

The molecular weight of the living polymer may be controlled by adjusting the molar ratio of the monomer to the initiator.

The coupling reaction of the living polymer with the backbone polymer may be carried out at a temperature of $-30°$ to $+100°$ C., preferably from: $-30°$ to $+70°$ C. in the atmosphere of an inert gas or under high vacuum in an inert organic solvent as described above. The reaction time may vary from 1 to 72 hours depending upon other reaction conditions.

The number of side chains coupled to the backbone polymer may be controlled by adjusting the density of pendant vinylidene groups in the backbone polymer and the molar ratio of the living polymer to the backbone polymer.

The resulting copolymer thus prepared has a unique configuration in which a plurality of polymer side chains extend from the middle of the backbone polymer. It is for this reason that the graft copolymer of the present invention has a viscosity lower than that of a straight chain linear polymer having a corresponding molecular weight and, therefore, is useful as a vehicle resin for use in formulating high-solids coating compositions. The graft copolymer is also useful as an adhesive because of its large free volume. Since substantially no homopolymer is formed, the overall production steps may be greatly simplified.

The following examples are offered for illustrative purposes only. All parts and percents therein are by weight unless otherwise indicated.

In these examples, various parameters of polymeric products were determined as follows. Polymer molecular weights and molecular weight distribution were determined using a differential refractometer, UV spectrophotometer, GPC provided with laser small angle nephelometer, osmotic pressure osmometer, vapor pressure osmometer and ultracentrifugation. Polymer compositions were determined by 1H-NMR, 13C-NMR or by means of the above GPC. The metallized percent of the backbone polymer was determined by 1H-NMR after coupling trimethylchlorosilane to the activated site of the backbone polymer followed by isolating the coupled product in pure form. The hydroxy and acid numbers of hydroxy or carboxy terminated copolymers were determined by IR spectrophotometry, titration with KOH, ASTM E222-66 method, Zerewitinoff's method or 1H-NMR of silylated products.

SYNTHESIS OF 1-PHENYL-1-(4-VINYLPHENYL) ETHYLENE (PVPE)

Example 1

To a 2 liter flask equipped with a stirrer, a reflux condenser and a drip funnel was placed 24.8 g of magnesium powder. To the flask were added dropwise 424 ml of tetrahydrofuran and 120 ml of p-chlorostyrene. The mixture was allowed to react at $65°$ C. to prepare a Grignard reagent and cooled to $30°$ C. Then 100 ml of tetrahydrofuran and 106 ml of acetophenone were added dropwise and allowed to react. After the completion of the reaction, 20 ml of concentrated HCl in 500 ml of water were added. The reaction mixture was extracted with ethyl ether and the extract was evaporated to dryness to obtain an alcohol corresponding to PVPE. PVPE was obtained by dehydrating this alcohol with potassium hydrogen sulfate followed by distillation in vacuo. Yield was 50% of theory.

The product was identified by IR sectrum, 1H-NMR, 13C-NMR and gas chromatography.

ANION POLYMERIZATION OF PVPE

Example 2

Using the high vacuum break-seal method, a flask was charged with an amount of fully dehydrated benzene and a solution of sec-butyl lithium in heptane. Then an amount of a solution of PVPE in benzene (about 10 v/v% concentration) was added thereto. After a certain length of time, the polymerization reaction was stopped by the addition of a small amount of methanol. The resulting polymer was purified by precipitating from benzene methanol mixture repeatedly and dried in vacuo. The reaction conditions, number average molecular weight Mn referenced to polystyrene and yield are shown in Table 1.

TABLE 1

| Polymer No. | Initiator | (mmol) | PVPE (g) | Reaction time (hr.) | Conc. (v/v %) | Mn $\times 10^4$ | Yield (%) |
|---|---|---|---|---|---|---|---|
| 1-1 | Sec-BuLi | 0.076 | 4.1 | 0.5 | 4.0 | 0.6 | 4.9 |
| 1-2 | " | 0.076 | 3.8 | 7.0 | 3.4 | 1.0 | 11 |

CATION POLYMERIZATION OF PVPE

Example 3

To a 300 ml round flask equipped with a three way valve was placed an amount of an initiator in purified toluene under the atmosphere of nitrogen gas. Then an amount of PVPE in toluene was added. After a certain length of time, a small amount of methanol was added to stop the reaction. The resulting polymer was purified as in Example 2. Various data are shown in Table 2. In run No. 2-2, the monomer was gelled almost instantaneously.

TABLE 2

| Polymer No. | Initiator | (mmol) | PVPE (g) | Time (hr.) | Temp. °C. | Conc. (v/v %) | Yield (%) | Mn × $10^4$ |
|---|---|---|---|---|---|---|---|---|
| 2-1 | $BF_3OEt_2$ | 0.57 | 4.1 | 2.0 | 0 | 13.7 | 44 | 12 |
| 2-2 | $CF_3SO_3H$ | 0.57 | 5.1 | 0 | 0 | 17 | — | — |
| 2-3 | $CF_3SO_3H$ | 0.45 | 2.8 | 3.0 | −30 | 5.8 | 68 | 0.3 |

CATION POLYMERIZATION OF PVPE

Example 4

Using the high vacuum break-seal method, a flask was charged with an amount of a mixture of trifluoromethanesulfonic acid and fully dehydrated toluene. Then an amount of a solution of PVPE in toluene (about 10 v/v% concentration) was added. After a certain length of time, a small amount of methanol was added to stop the reaction. The resulting polymer was purified as in Example 2. Various data are shown in Table 3.

TABLE 3

| Polymer No. | Initiator (mmol) | PVPE (g) | Time (hr.) | Temp. °C. | Conc. (v/v %) | Mn × $10^4$ | Yield (%) |
|---|---|---|---|---|---|---|---|
| 3-1 | 0.21 | 5.8 | 2.5 | −30 | 4.2 | 0.32 | 21.0 |
| 3-2 | 0.27 | 5.7 | 6.0 | −10 | 4.4 | — | 99.3 |
| 3-3 | 0.20 | 6.5 | 6.0 | −20 | 5.1 | — | 89.3 |
| 3-4 | 0.24 | 10.1 | 17 | −30 | 4.2 | — | 100 |

CATION POLYMERIZATION OF PVPE AND STYRENE

EXAMPLE 5

Using the high vacuum break-seal method, a flask was charged with an amount of a mixture of trifluoromethanesulfonic acid and fully dehydrated toluene. Then an amount of a solution of PVPE and styrene in toluene (about 10 v/v% concentration) was added. After a certain length of time, a small amount of methanol was added to stop the reaction. The resulting polymer was purified as in the preceding examples. The reaction conditions, the number average molecular weight, yield and monomeric composition of the copolymer are shown in Table 4. The monomeric composition was determined by intrapolating the molar absorbance coefficient at 280 nm (PVPE homopolymer) on a standard curve for polymer blends of PVPE homopolymer and polystyrene at varying ratios.

CATION POLYMERIZATION OF PVPE AND P-METHYLSTYRENE

Example 6

Using the high vacuum break-seal method, a flask was charged with an amount of a mixture of trifluoromethanesulfonic acid and fully dehydrated toluene at −78° C. Then an amount of a solution of PVPE and p-methylstyrene in toluene (about 10 v/v% concentration) was added. After a certain length of time, a small amount of methanol was added to stop the reaction. The resulting polymer was purified as in the preceding examples. Various data are shown in Table 5.

TABLE 5

| Polymer No. | Initiator (mmol) | Monomer (g) PVPE | Monomer (g) p-MeSt | Time (hr.) | Conc. (v/v %) | Conversion rate (%) | Mn × $10^4$ | Mw/Mn | PVPE mol. ratio |
|---|---|---|---|---|---|---|---|---|---|
| 5-1 | 0.46 | 5.0 | 5.2 | 42 | 4.4 | — | Gel | — | — |
| 5-2 | 0.44 | 5.0 | 6.5 | 17 | 5.3 | 100 | 1.4 | 2.49 | 0.17 |
| 5-3 | 0.062 | 0.45 | 0.63 | 14 | 3.4 | 94 | Gel | — | — |
| 5-4 | 1.4 | 10.7 | 15.5 | 1 | 2.9 | 71 | 0.79 | 1.47 | 0.14 |
| 5-5 | 1.4 | 10.8 | 19.9 | 1 | 5.6 | 91 | 0.89 | 2.13 | 0.19 |

METALLIZATION OF PVPE POLYMER

Example 7

Using the high vacuum break-seal method, copolymer No. 5-2 of Example 6 was freeze-dried from benzene and then dissolved in toluene.

Using the high vacuum break-seal method again, a flask was charged with 14.7 ml of the above solution (0.75 g of polymer No. 5-2) and 2.9 ml of N-methylpyrrolidine (NMP) (9.4 times in molar concentration relative to n-BuLi). Then 1.85 ml of n-butyl lithium (1.85 equivalents relative to —C=C—) was added and allowed to react at room temperature for 3 hours. A 5 ml aliquot taken from the reaction mixture was reacted with 3 ml of trimethylchlorosilane to obtain a silylated product. From the $^1$H-NMR (270 MHz) analysis of this product, the ratio of the peake intensity of trimethylsilyl group at about 0 ppm (S) to that of benzene proton at about 6–7 ppm (P) and the ratio of methy group in n-butyl group at about 1 ppm (B) to the peak intensity (P) were calculated. These ratios S/P and B/P were 0.15 and 0.16, respectively. These values are close to the PVPE unit content of polymer No. 5-2 of 0.17. The number average molecular weight of the silylated polymer by the GPC analysis was 2.26×$10^4$ and the molecular distribution Mw/Mn was 3.43.

TABLE 4

| Polymer No. | Initiator (mmol) | Monomer (g) PVPE | Monomer (g) Styrene | Time (hr.) | Temp. °C. | Conc. (v/v %) | Mn × $10^4$ | Conversion rate (%) | PVPE mol. ratio Cal'd | PVPE mol. ratio Found |
|---|---|---|---|---|---|---|---|---|---|---|
| 4-1 | 0.61 | 4.3 | 12.0 | 16 | −35 | 3.4 | 0.44 | 100 | 0.182 | 0.154 |
| 4-2 | 0.49 | 10.7 | 19.1 | 17 | −30 | 5.4 | 0.20 | 75 | 0.238 | 0.348 |
| 4-3 | 0.48 | 9.3 | 12.8 | 15 | −30 | 4.3 | 0.42 | 100 | 0.367 | — |

Examples 8–15

Starting from polymer Nos. 5-2, 5-4 and 5-5, respectively, Example 7 was repeated at various conditions shown in Table 6. The results are also shown in Table 6.

TABLE 6

| Example No. | Polymer No. | n-BuLi/-c≡c- | NMP/n-BuLi | Temp. °C. | Conc. (w/v %) | S/P | B/P | Mn × $10^4$ | Mw/Mn |
|---|---|---|---|---|---|---|---|---|---|
| 8 | 5-2 | 0.75 | 13.5 | R.T. | 3.1 | — | — | 5.33 | 7.33 |
| 9 | 5-4 | 3.54 | 10.4 | R.T. | 3.3 | 0.14 | 0.14 | 1.00 | 1.57 |
| 10 | 5-4 | 0.92 | 11.9 | R.T. | 3.6 | 0.05 | 0.04 | 1.41 | 2.89 |
| 11 | 5-5 | 0.72 | 11.3 | 0 | 4.3 | 0.08 | 0.05 | 1.88 | 4.08 |
| 12 | 5-5 | 1.44 | 11.4 | 0 | 3.5 | 0.09 | 0.10 | 1.23 | 2.57 |
| 13 | 5-5 | 4.90 | 10.2 | 0 | 3.5 | 0.16 | 0.15 | 0.91 | 2.14 |
| 14 | 5-5 | 0.91 | 0 | 0 | 4.9 | — | — | gel | — |
| 15 | 5-5 | 1.00 | 18.8 | 0 | 4.6 | 0.14 | 0.15 | 1.25 | 2.39 |

GRAFT POLYMERIZATION

Example 16

Using the high vacuum break-seal method, a flask was charged with 16.4 ml of a solution of metallized polymer No. 5-5 of Example 15 in toluene (0.75 g of metallized polymer), 30 ml of fully dehydrated toluene and 30 ml of a toluene solution of lithium benzyloxide (1.2 equivalents relative to the metallized site). Then 6.0 ml of methyl methacrylate (MMA) was added and allowed to react at −78° C. for 1 hour. Then 6.6 ml of ethylene oxide was reacted for 30 minutes. The reaction mixture was then poured into methanol whereupon 6.1 g (95% of theory) of a graft copolymer was obtained.

The number average molecular weights of this graft copolymer and of each its side chain polymer calculated from the charged amount of MMA and the concentration of metallized site were $1.1 \times 10^5$ and $6.7 \times 10^3$, respectively.

By the GPC analysis of this graft copolymer, a response to UV spectrophotometer at 254 nm corresponding to a response to differential refractometer was observed. This confirms the production of a graft copolymer. The apparent Mn and Mw/Mn were $5.2 \times 10^4$ and 5.3, respectively.

A peak corresponding to poly MMA was not found in the supernatant from which the graft copolymer was reprecipitated.

The $^1$H-NMR analysis of the graft copolymer revealed that the tacticity of the side chain polymer (syndiotactic/heterotactic/isotactic) was 6.7/16.6/76.8. The number average molecular weight of the side chain polymer was estimated to be $6.2 \times 10^3$ based on the peak intensity ratio of benzene proton to methoxy group of poly MMA by $^1$H-NMR analysis and the concentration of metallized site of the starting polymer.

An absorption of OH was found at about 3500 cm$^{-1}$ in the IR spetrophotometry of the graft copolymer.

EXAMPLE 17

Using the high vacuum break-seal method, a flask was charged with 12.6 ml of a solution of metallized polymer No. 5-5 of Example 15 in toluene (0.58 g of metallized polymer), 30 ml of fully dehydrated toluene and 77 ml of a toluene solution of lithium benzyloxide (5.5 equivalents relative to the metallized site). Then 6.75 ml of MMA was added and allowed to react at −78° C. for 15 minutes. Then 3.8 ml of ethylene oxide was reacted for 1 hour. The reaction mixture was then poured into methanol whereupon 7.0 g (100% of theory) of a graft copolymer was obtained.

The number average molecular weights of this graft copolymer and of each its side chain polymer calculated as in Example 16 were $9.7 \times 10^3$ and $1.5 \times 10^5$, respectively.

By the GPC analysis of this graft copolymer, a response to UV spectrophotometer at 254 nm corresponding to a response to differential refractometer was observed. This confirms the production of a graft copolymer.

A peak corresponding to poly MMA was not found in the supernatant from which the graft copolymer was reprecipitated. The apparent Mn and Mw/Mn were $6.9 \times 10^4$ and 5.8, respectively.

The $^1$H-NMR analysis of the graft copolymer revealed that the tacticity of the side chain polymer (sydiotactic/heterotactic/isotactic) was 3.3/9.0/88.2. The number average molecular weight of the side chain polymer was estimated to be $9.5 \times 10^3$ by the same method as described in Example 16.

An absorption of OH was found at about 3500 cm$^{-1}$ in the IR spectrophotometry of the graft copolymer.

We claim:

1. A graft copolymer having a backbone polymer segment and a plurality of polymer side chains grafted to said backbone polymer segment, wherein said backbone polymer is a polymer having a plurality of pendant vinylidene groups consisting essentially of (a) 0.1 to 100 mole % of a recurring unit of the formula:

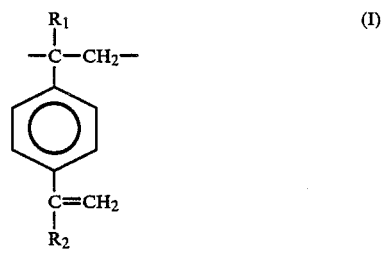

(I)

wherein $R_1$ is H or $C_1$–$C_4$ alkyl; and $R_2$ is $C_2$–$C_{10}$ alkyl or alkoxy, unsubstituted or substituted phenyl, or tri-($C_1$–$C_4$ alkyl)silyl; and (b) 0 to 99.9 mole % of (i) a recurring unit of the formula

(II)

wherein $R_1$ is as defined, $R_3$ is $C_1$–$C_4$ alkyl or alkoxy, or unsubstituted or substituted phenyl; (ii) a recurring unit of the formula:

$$-CH_2-\overset{\overset{R_4}{|}}{C}=CH-CH_2- \quad \text{(III)}$$

wherein $R_4$ is H, $C_1$–$C_4$ alkyl or halogen; (iii) a position isomer of the unit of the formula (III); or (iv) a mixture of said units (II), (III) or its position isomer, said polymer having a number average molecular weight of 1000, to 1,000,000, and wherein each of said polymer side chains consists essentially of a polymer of an ethylenically unsaturated monomer capable of anion polymerization having a number average molecular weight from 500 to 1,000,000 per chain, said polymer side chains being grafted to said backbone polymer and said plurality of pendant vinylidene groups, and said polymer side chains being terminated with a functional group capable of crosslinking.

2. The polymer according to claim 1, wherein said unit (a) is derived from 1-phenyl-1-(4-vinylphenyl)ethylene and said unit (b) is derived from styrene or p-methylstyrene.

3. The graft copolymer according to claim 1, wherein said ethylenically unsaturated monomer is an ester or nitrile of (meth)acrylic acid, styrene or a derivative thereof or a diene monomer.

4. A method for producing a graft copolymer which comprises the steps of reacting the polymer having a plurality of pendant vinylidene groups consisting essentially of (a) 0.1 to 100 mole % of a recurring unit of the formula:

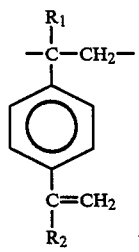

wherein $R_1$ is H or $C_1$–$C_4$ alkyl; and $R_2$ is $C_2$–$C_{10}$ alkyl or alkoxy, unsubstituted or substituted phenyl, or tri-($C_1$–$C_4$ alkyl)silyl; and (b) 0 to 99.9 mole % of (i) a recurring unit of the formula $$-\overset{\overset{R_1}{|}}{\underset{\underset{R_3}{|}}{C}}-CH_2- \quad \text{(II)}$$

wherein $R_1$ is as defined, $R_3$ is $C_1$–$C_4$ alkyl or alkoxy, or unsubstituted or substituted phenyl; (ii) a recurring unit of the formula:

$$-CH_2-\overset{\overset{R_4}{|}}{C}=CH-CH_2- \quad \text{(III)}$$

wherein $R_4$ is H, $C_1$–$C_4$ alkyl or halogen; (iii) a position isomer of the unit of the formula (III); or (iv) a mixture of said units (II), (III) or its position isomer, said polymer having a number average molecular weight of 1,000 to 1,000,000, with a compound of the formula $MR_5$, wherein M is a metal of group Ia in the periodic table and $R_5$ is a hydrocarbon radical, to metallize said pendant vinylidene groups, polymerizing an ethylenically unsaturated monomer in the presence of said metallized polymer as an anionic polymerization initiator to produce a graft copolymer having a plurality of polymer side chains each having a number average molecular weight from 500 to 1,000,000, and reacting said graft copolymer with a reagent capable of introducing a functional group at the terminal of each of said polymer side chains.

5. The method according to claim 4, wherein said ethylenically unsaturated monomer is an ester or nitrile of (meth)acrylic acid, styrene or a derivative thereof or a diene monomer.

6. The method according to claim 4, wherein said anion polymerization is carried out in the presence of an alkali metal alkoxide.

7. The method according to claim 4, wherein said metallizing step is carried out in the presence of a tertiary monoamine.

8. The method according to claim 4, wherein said unit (a) is derived from 1-phenyl-1-(4-vinylphenyl)ethylene and said unit (b) is derived from styrene or p-methylstyrene.

* * * * *

UNITED STATES PATENT AND TRADEMARK OFFICE
CERTIFICATE OF CORRECTION

PATENT NO. : 4,853,436
DATED : AUGUST 1, 1989
INVENTOR(S) : OHATA ET AL

It is certified that error appears in the above-identified patent and that said Letters Patent is hereby corrected as shown below:

Title page, third inventors name: reads "Ikedal Shoji"

should read -- Ikeda Shoji --

Signed and Sealed this

Twenty-second Day of May, 1990

*Attest:*

HARRY F. MANBECK, JR.

*Attesting Officer*        *Commissioner of Patents and Trademarks*